United States Patent
Cholewa

(10) Patent No.: US 6,531,061 B1
(45) Date of Patent: Mar. 11, 2003

(54) DISPOSABLE DIALYSIS CASSETTE

(76) Inventor: Olivia M. Cholewa, 609 Eagle Heights, Apt. E, Madison, WI (US) 53705

( * ) Notice: Subject to any disclaimer, the term of this patent is extended or adjusted under 35 U.S.C. 154(b) by 0 days.

(21) Appl. No.: 09/619,459

(22) Filed: Jul. 19, 2000

Related U.S. Application Data

(60) Provisional application No. 60/144,805, filed on Jul. 21, 1999.

(51) Int. Cl.$^7$ .......................... B01D 61/24; B01D 63/00
(52) U.S. Cl. ..................... 210/232; 210/227; 210/231; 210/321.6
(58) Field of Search ............................. 210/227, 228, 210/230, 231, 232, 321.6, 321.72, 321.75, 321.78, 321.84, 321.87

(56) References Cited

U.S. PATENT DOCUMENTS

| | | | |
|---|---|---|---|
| 3,679,059 A | 7/1972 | Wyatt et al. ................ | 210/541 |
| 3,696,931 A | 10/1972 | Hough ........................ | 210/244 |
| 4,828,706 A | 5/1989 | Eddleman ................... | 210/644 |
| 4,865,813 A | 9/1989 | Leon .......................... | 422/101 |
| 5,185,048 A | 2/1993 | Guerif ..................... | 210/321.6 |
| 5,324,428 A | 6/1994 | Flaherty ..................... | 210/232 |
| 5,342,517 A | 8/1994 | Kopf .......................... | 210/228 |
| 5,503,741 A | 4/1996 | Clark ......................... | 210/232 |
| 5,783,075 A | 7/1998 | Eddleman et al. .......... | 210/232 |

Primary Examiner—John Kim
(74) Attorney, Agent, or Firm—Quarles & Brady LLP

(57) ABSTRACT

Disclosed is a disposable dialysis cassette which is flat, flexible, self-closing and applicable to solutions containing proteins, DNA, RNA, or other molecules. The dialysis cassette embodies a first and second semi-permeable dialysis membrane, or tubular dialysis membrane, sealed by a flexible frame to form a dialysis chamber having a self-closing channel for the introduction of a dialysis sample by either a pipette or other dispensing mechanism.

22 Claims, 2 Drawing Sheets

DISPOSABLE DIALYSIS CASSETTE

CROSS-REFERENCE TO RELATED APPLICATIONS

This application claims priority from provisional patent application Ser. No. 60/144,805, filed Jul. 21, 1999.

STATEMENT REGARDING FEDERALLY SPONSORED RESEARCH OR DEVELOPMENT

Not applicable.

BACKGROUND OF THE INVENTION

The present invention relates to a holder for a dialysis membrane used in osmotic separation. More specifically, the present invention discloses a dialysis support frame.

Dialysis separation is an effective means of separating molecules according to their ability to diffuse through a semi-permeable membrane. The dialysis solution is placed within a dialysis chamber containing one or more walls formed by a semi-permeable membrane. The membrane, by virtue of its composition and porosity, allows molecules equal to or less than a particular molecular weight to pass through and into a dialysis bath in which the chamber is submerged. The driving force behind dialysis separation lies within the osmotic flow created by the concentration differential between the dialysis solution and the dialysis bath.

Although dialysis separation is an effective means of separating molecules of variable sizes, it is cumbersome and generally requires great care to avoid contamination or the loss of a sample. A commonly applied method involves sealing the top and bottom ends of a tubular dialysis membrane with clips or collars to form a dialysis chamber. If the ends of the tubing are not carefully sealed, the dialysis chamber will leak and the sample may be lost. In addition, the lack of support for the generally flaccid membrane results in significant difficulty in loading and unloading samples. Because of the nature of the clips and collars used to seal the dialysis chamber, it is often necessary to handle the membrane which may effect the integrity of the membrane thus causing inefficient dialysis separation.

Finally, this method does not provide ample space for labeling the chamber to indicate the enclosed sample. Therefore, labeling must be written on the small clamp or collar, or on an object which is inconveniently attached to the tubing with material such as string.

U.S. Pat. No. 5,788,075 describes an apparatus containing a floating support ring comprising a central opening surrounded by a downwardly extending tube used to support a dialysis membrane. The walls of the apparatus and the floor of the dialysis membrane converge to create the dialysis chamber. In its operation, the assembled apparatus is suspended over a dialysis bath and the sample loaded into the dialysis chamber.

Although this solution offers advantages, it introduces new problems. First, the sample is open to the air which allows it to be easily contaminated. Secondly, because the vessel is open, it is easy for the sample to spill into the dialysis bath as it floats. Loading and unloading are greatly simplified, but assembly of the device requires some skill by the user.

U.S. Pat. No. 5,503,741, describes a dialysis cassette which embodies a hermetically sealed sample chamber formed by fixing two dialysis membranes to a gasket. The gasket is impermeable to the sample being dialyzed, but is penetrable by a hypodermic needle. Upon assembly, the sealed sample chamber is contained within a rigid housing containing windows exposing the dialysis membranes. In its operation, a hypodermic needle is inserted through the gasket and into the chamber so as to insert or withdraw the dialysis solution. The cassette is then placed within a dialysis bath where dialysis separation occurs.

Unfortunately, this product also has several drawbacks. One such drawback is the fact that the device requires the use of a hypodermic needle to introduce the dialysis solution into the dialysis chamber. The use of a hypodermic needle may be unacceptable when the dialysis cassette is used to separate DNA or RNA fragments as high shear forces are created in the liquid passing through the needle such as may damage larger molecules. The shear forces may also disrupt and inhibit the dialysis of whole mammalian cells, algal cells, protists (i.e., amoebas, water bears, etc.), and colonial organisms.

The dialysis cassette has a further drawback in that it requires greater skill in the loading and unloading of samples, as compared to the methods described above. Furthermore, in view of its construction, the dialysis cassette is likely to carry a greater expense in its use.

What is needed is a simplified device providing minimal risk of contamination or sample loss. This device should allow for the dialysis of delicate samples which include proteins, DNA or RNA.

BRIEF SUMMARY OF THE INVENTION

The present invention provides a simplified disposable dialysis cassette in which a flexible frame supports and exposes a dialysis membrane for simplified filling and handling.

The dialysis cassette embodies a first and second semi-permeable dialysis membrane, or tubular dialysis membrane sealed by a flexible frame to form a dialysis chamber having a self-closing channel for the introduction of samples by either a pipette or other dispensing mechanism. The dialysis cassette is assembled by the combination of a first and second flexible polymeric sheet bonded together to form a semi-rigid frame, wherein the bottom end of the dialysis chamber is preferably affixed and sealed within the semi-rigid frame and the top end of the dialysis chamber is extended within and to the edge of the semi-rigid frame to create a self-closing channel which provides access to a portion of the dialysis chamber exposed by a window formed by central apertures contained within the first and second polymeric sheets. In its use, the frame may be flexed to allow the opening and closing of the self-closing channel for the introduction of a sample into the dialysis chamber.

In a further embodiment of the invention, an instrument guide is affixed within the channel to allow for the easy insertion of a pipette or other dispensing mechanism used to deposit the dialysis sample.

It is an object of the present invention to provide a disposable dialysis cassette which is less bulky, flexible, self-closing and capable of separating sensitive molecules such as protein, DNA, RNA or other large, linear polymers not of biological origin that can be broken by shear force. It is also an object of the present invention to provide a flexible dialysis cassette, wherein the semi-rigid frame allows the dialysis chamber to be self-closing.

It is another object of the invention to provide a flexible cassette which is useful in culter systems designed for certain tissues, algaes, and microbial organisms.

Other objects, advantages, and features of the present invention will become apparent after examination of the specification, claims, and drawings.

DETAILED DESCRIPTION OF THE PREFERRED EMBODIMENT

Figure 2:
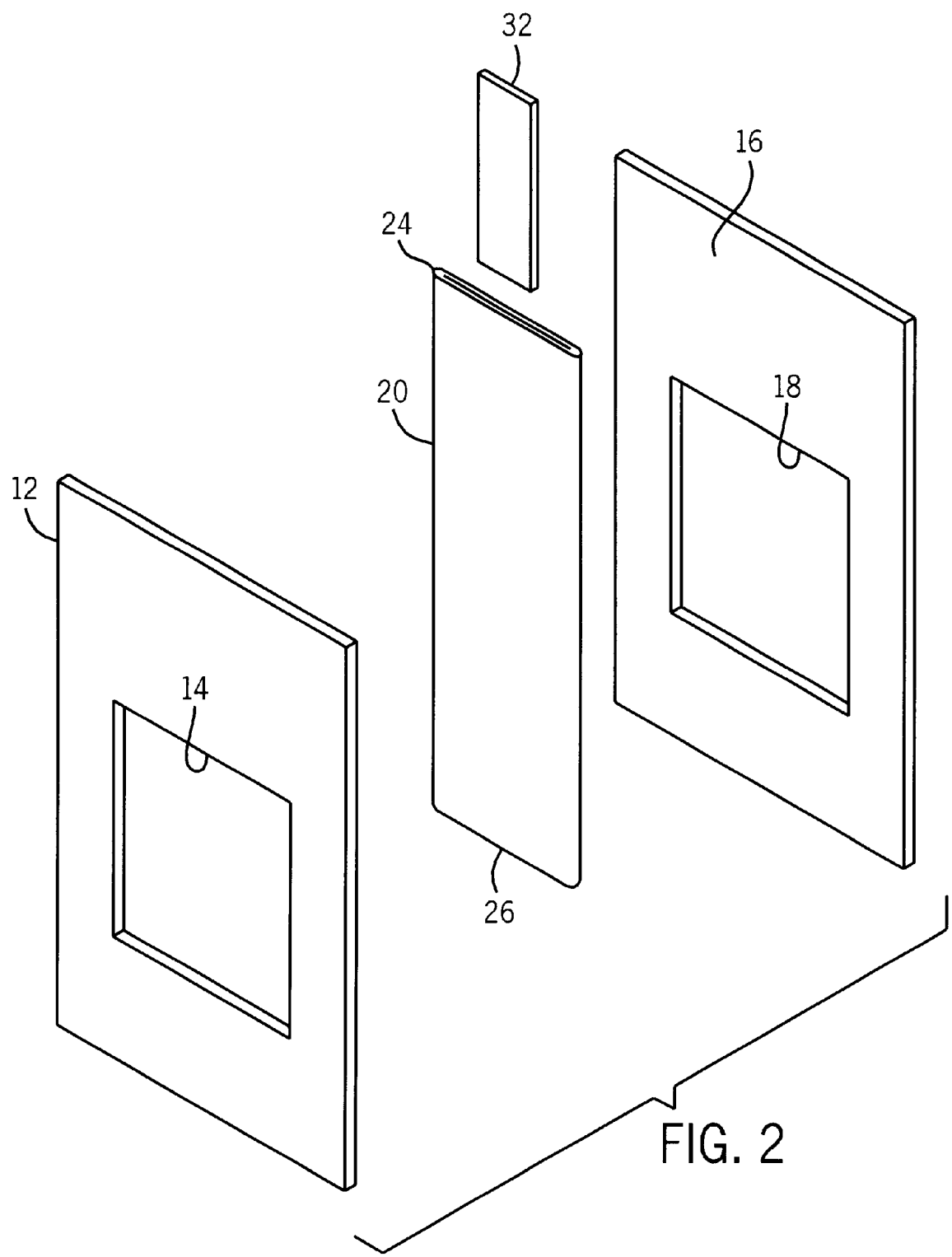
FIG. 2 is an exploded perspective view showing the dialysis cassette in a disassembled relationship.

Referring to FIG. 2, the dialysis cassette 10 includes a first generally planar, rectangular flexible mounting sheet 12 having a rectangular central aperture 14 and a matching second generally planar, flexible mounting sheet 16 having a matching central aperture 18. The first and second flexible mounting sheets 12 and 16 are bonded together about a dialysis chamber 20 to form a semi-rigid frame 22. The frame 22 is semi-rigid in that it maintains a rigid state when standing alone or when placed within a dialysis bath, but that it may be flexed by bending with a hand or other device.

The dialysis chamber 20 is defined as a vacant cavity wherein the walls are of at least one semipermeable dialysis membrane sealed to form a chamber having a top end 24 and a bottom end 26. The semipermeable dialysis membrane used is preferably any one of the customary dialysis membranes well known in the art. These membranes are commonly derived from regenerated cellulose and vary based upon the size of the pores contained therein. The size of the pores determines what solutes pass through the membrane and an appropriate pore size would be selected depending upon the size of solute to be removed. In the preferred embodiment, the dialysis chamber 20 comprises of a tubular dialysis membrane. The tubular dialysis membrane provides a hermetically sealed chamber and is typically formed from a cellulosic material such as regenerated cellulose derived from cotton linters. In a second embodiment, the dialysis chamber 20 comprises of a first and second semipermeable dialysis membrane sealed together to form the vacant dialysis chamber. The porosity of these two membranes may either differ or be the same depending on the desired use of the dialysis cassette. Preferably, the dialysis chamber 20, central apertures 14 and 18, and mounting sheets 12 and 16 are generally rectangular in shape, however, they may also be of any other geometrical shape consistent with the desired use of the invention.

Figure 1:
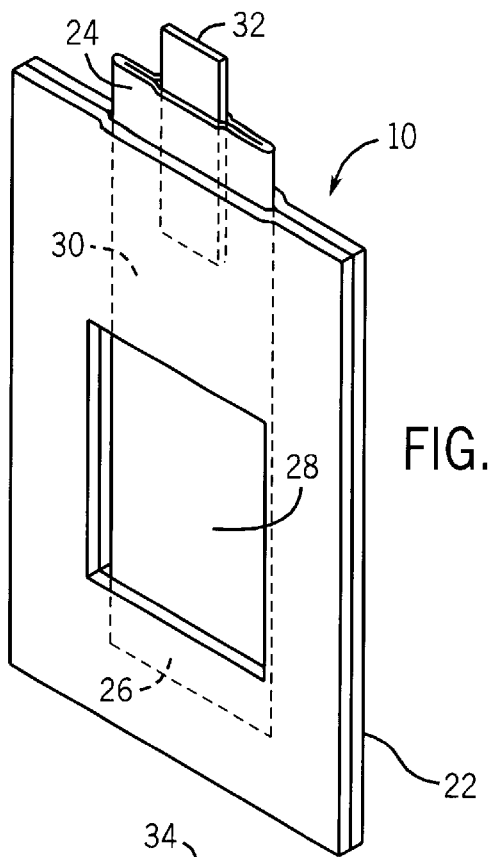
FIG. 1 is a perspective view of the dialysis cassette.
Figure 3:
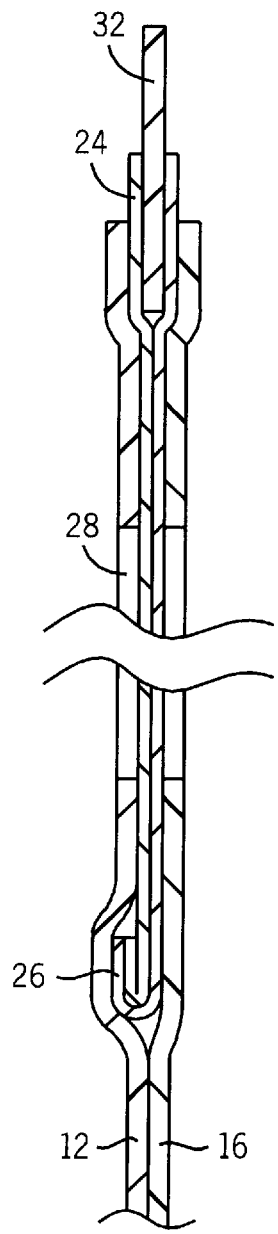
FIG. 3 is a cross-sectional side view of the dialysis cassette.

In its assembled form, FIG. 1, the window created by central apertures 14 and 18 circumscribes and exposes a portion of the dialysis chamber 20 to form a separation chamber 28 which is accessible by a channel 30 formed by the extension of the top end 24 of dialysis chamber 20 in between and beyond the mounting sheets 12 and 16. The bottom end 26 is extended beyond the central apertures 14 and 18, away from the channel 30, and in between the mounting sheets 12 and 16. Preferably, the bottom end 26 is folded and secured within the mounting sheets 12 and 16 in a fashion to seal the dialysis chamber 20 and avoid leakage of the sample, FIG. 3.

The portion of the mounting sheets 12 and 16, defined by the channel 30, which do not bind together because of the presence of the dialysis chamber, maintain a substantial degree of linear torsion such that it creates a self-closing mechanism in channel 30. Accordingly, the channel 30 is maintained in a closed configuration such that access is impeded to the separation chamber 28 unless the channel is opened by the insertion of a pipette or other dispensing mechanism.

Figure 4:
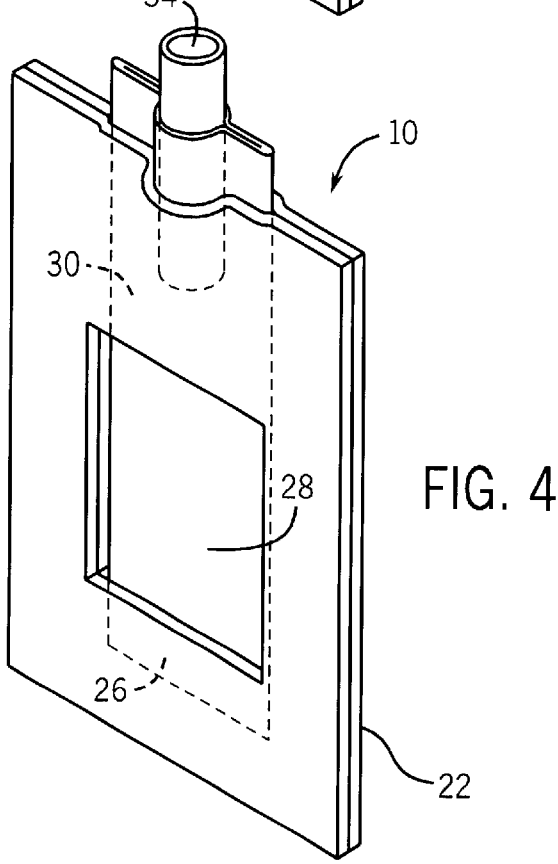
FIG. 4 is a perspective view of the dialysis cassette using a straw as the instrument guide.

In the preferred embodiment of the present invention, an instrument guide 32 is inserted within the channel 30 and affixed to one of the mounting sheets 12 or 16 through the semipermeable dialysis membrane of the dialysis chamber 20 so that a portion of the guide is within and without the semi-rigid frame 22. The instrument guide 32 is provided to assist in the introduction of a pipette or dispensing mechanism through the self-closing channel 30, without tearing the semipermeable dialysis membrane, and into the separation chamber 28 where a sample is deposited. The instrument guide 32 is preferable a generally planar, rectangular strip of a polymeric sheet and constructed of the same material as the mounting sheets 12 and 16. However, the instrument guide may also include, but is not limited to, a straw 34 or other objects consistent with the desired use of the invention, FIG. 4.

An important aspect of the present invention is that the channel 30 is accessible by a pipette or dispensing mechanism. The flexible nature of the frame 22 formed by the mounting sheets 12 and 16 and the extension of the top end 24 of the dialysis chamber 20 provides a natural channel for introduction of the dialysis sample. This is important because it allows the dialysis of a solution containing large linear biomolecules such as DNA or RNA strands, which are often sheared when injected through a hypodermic needle. The natural channel also allows the dialysis of large, linear polymers of nonbiological origin that are susceptible to breaking by shear force.

The flexible mounting sheets 12 and 16 are preferably polymeric sheets of the kind normally found in lamination processes. However, the mounting sheets may also include, but is not limited to, any other generally planar sheet made of a polymer material known in the art which, by its nature, is flexible and remains semi-rigid when bonded to another generally planar, polymer sheet. The flexible sheets are bonded together using any method which does not interfere with the flexibility of the frame or degrade the membrane forming the dialysis chamber. Such methods are commonly known in the art and include, but are not limited to, bonding by heat or by an adhesive.

In use, a sample is loaded into the device by sliding a pipette or other dispensing mechanism along the instrument guide 32 and through the channel 30 causing the channel 30 to open. Once the pipette or other dispensing mechanism passes through the self-closing channel 30 the dialysis sample is deposited within the separation chamber 28 and the pipette or other dispensing mechanism is removed. To effectively seal the dialysis cassette, a clamp is placed over the top end 24 of the dialysis chamber 20 and the dialysis cassette 10 is submerged in a dialysis bath where dialysis separation takes place. Preferably, said clamp is constructed of a polymer having a density less than that of the dialysis bath so as to allow the dialysis cassette to float in a vertical orientation. In the alternative, a clamp comprising a float, such as Styrofoam or any other float known in the art, may be used to achieve the same result. After the dialysis of the sample is complete, the dialysis cassette is removed from the dialysis bath. The treated sample may be readily removed after dialysis simply be removing the clamp and reinserting a pipette or other dispensing mechanism into the dialysis chamber. Upon completion, the dialysis cassette may be thrown away.

An example of the use of the device described above would be the exchange of a buffer, in which a protein or DNA sample reside, for another buffer. The protein or DNA buffer "A" would be injected into the dialysis chamber of the device and then the device would be submerged into a buffer "B" dialysate which is contained in a vessel such as a beaker. The protein or DNA being larger than the dialysis membrane pores would be retained within the sample chamber, while the buffer molecules within the sample chamber would exchange by diffusion with the buffer molecules in the dialysate. Samples are loaded and unloaded with a pipette or straw mechanism during the process and fingers only come into contact with the flexible frame surrounding the dialysis chamber and not the membrane itself. Because the device is semi-rigid and the dialysis chamber is enclosed, the spilling of a sample is improbable. The flexible frame surrounding the sample chamber is of ample size which allows for the easy labeling of the cassette with commonly used scientific marking pens. The construction of the current invention provides a higher surface to volume ratio of the dialysis chamber which results in faster dialysis times.

Because of the disclosed invention's thin and flexible nature, the dialysis cassette is also capable of use in a chamber for microdialysis. For example, a dialysis cassette may be constructed containing first and second semipermeable membranes of differing porosity. The entire dialysis cassette may then be inserted between two separate chambers containing two distinct dialysis solutions. A sample introduced into the chamber will then be separated by microdialysis into three distinct samples according to the ability of its elements to pass through the respective membrane. The desired product may then be collected and used accordingly.

The overall flat design of the cassette also allows good light penetration and rapid diffusion of nutrients, waste, and other biological products. Accordingly, the dialysis cassette may be useful in certain culture systems. For example, the cassette may be used in culturing algae that cannot be grown on solid media. The cassette may also find use in cultering microbial organisms that require rapid exchange of growth environment, either to remove accumulation of inhibitory metabolites or rapid removal of waste products. Finally, the cassette may be useful in various tissue cultures wherein the cells are limited to a certain cell depth.

The present invention is not limited to the foregoing embodiments and examples, but is intended to encompass all such variations and modifications as come within the scope of the appended claims.

I claim:

1. A dialysis cassette comprising:
   a semipermeable dialysis membrane defining a cavity having a first end and a second end;
   a first and second flexible mounting sheet having a central aperture, said sheets being bonded together to form a semi-rigid frame about the semipermeable membrane, wherein the aperture circumscribes and exposes a portion of the semipermeable membrane, and wherein the first end is secured between the first and second mounting sheets, and wherein the second end extends between and to at least the edge of the semi-rigid frame formed by the bonding of the first and second flexible mounting sheets to form a channel; and
   whereby a portion of the semi-rigid frame defined by the channel maintains a substantial degree of linear torsion to create a self-closing mechanism in the channel and whereby the frame may be flexed about the channel to allow opening of the channel for the introduction of a sample into the cavity.

2. The dialysis cassette of claim 1 further including an instrument guide affixed to and inserted into the channel so that a portion of the guide is within and a portion of the guide is outside the frame formed by the bonding of the first and second mounting sheets.

3. The dialysis cassette of claim 2, wherein the instrument guide is of the same material as the mounting sheets.

4. The dialysis cassette of claim 2, wherein the instrument guide is selected from the group consisting of a strip and a straw.

5. The dialysis cassette of claim 1, wherein the semipermeable membrane is a tubular membrane having an open first end and an open second end.

6. The dialysis cassette of claim 1, wherein the semipermeable membrane is sealed together with a second semipermeable membrane to define the cavity.

7. The dialysis cassette of claim 1, wherein the flexible mounting sheet is a flexible polymeric sheet.

8. The dialysis cassette of claim 1, wherein the first and second mounting sheets are bonded together by heat sealing.

9. The dialysis cassette of claim 1, wherein the first and second mounting sheets are bonded together by an adhesive.

10. A dialysis cassette comprising:
    a semipermeable dialysis membrane defining a cavity having a first end and a second end;
    a first and second flexible mounting sheet having a central aperture, said sheets being bonded together to form a semi-rigid frame about the semipermeable membrane, wherein the aperture circumscribes and exposes a portion of the semipermeable membrane, and wherein the second end extends between and to at least the edge of the semi-rigid frame to form a channel between the first and second flexible mounting sheets; and
    whereby a portion of the semi-rigid frame defined by the channel maintains a substantial degree of linear torsion to create a self-closing mechanism in the channel and whereby the frame may be flexed about the channel to allow opening of the channel for the introduction of a sample into the cavity.

11. The dialysis cassette of claim 10 further including an instrument guide affixed to and inserted into the channel so that a portion of the guide is within and a portion of the guide is outside the frame formed by the bonding of the first and second mounting sheets.

12. The dialysis cassette of claim 11, wherein the instrument guide is of the same material as the mounting sheets.

13. The dialysis cassette of claim 11, wherein the instrument guide is selected from the group consisting of a strip and a straw.

14. The dialysis cassette of claim 10, wherein the semipermeable membrane is a tubular membrane having an open first end and an open second end.

15. The dialysis cassette of claim 10, wherein the semipermeable membrane is sealed together with a second semipermeable membrane to form the cavity.

16. The dialysis cassette of claim 10, wherein the flexible mounting sheet is a flexible polymeric sheet.

17. The dialysis cassette of claim 10, wherein the first and second mounting sheets are bonded together by heat sealing.

18. The dialysis cassette of claim 10, wherein the first and second mounting sheets are bonded together by an adhesive.

19. A dialysis cassette comprising:
  a tubular semipermeable dialysis membrane defining a cavity having an open first end and an open second end;
  a first and second flexible polymeric sheet having a central aperture, said sheets being bonded together about the tubular membrane to form a semi-rigid frame about the tubular membrane, wherein the aperture circumscribes and exposes a portion of the tubular membrane, and wherein the open first end of the tubular membrane is closed and secured in the frame, and wherein the second end of the tubular membrane is extended within and to at least the edge of the frame to form a channel; and
  wherein a portion of the semi-rigid frame defined by the channel maintains a substantial degree of linear torsion to create a self-closing mechanism in the channel and whereby the frame may be flexed about the channel to allow opening of the channel for the introduction of a sample into the cavity.

20. The dialysis cassette of claim 19, further including an instrument guide affixed to and inserted into the channel so that a portion of the guide is within and a portion of the guide is without the semi-rigid frame formed by the bonding of the first and second sheets.

21. The dialysis cassette of claim 20, wherein the instrument guide is of the same material as the polymeric sheets.

22. The dialysis cassette of claim 20, wherein the instrument guide is selected from the group consisting of a strip and a straw.

* * * * *